United States Patent [19]

Westerhoff

[11] Patent Number: 5,405,935
[45] Date of Patent: Apr. 11, 1995

[54] NON-VOLATILE SOLVENT REPLACEMENT

[76] Inventor: David Westerhoff, P.O. Box 1192 Goose Creek La., Middleburg, Va. 22117

[21] Appl. No.: 162,454

[22] Filed: Dec. 3, 1993

[51] Int. Cl.$^6$ .................. C08G 63/78; C08G 63/82; C07D 309/32; C07B 41/12
[52] U.S. Cl. .................. 528/277; 528/357; 549/231; 549/274; 554/24; 554/30; 554/31; 526/266
[58] Field of Search ............ 554/24, 30, 31; 549/231, 274, 415, 448; 528/277, 357

[56] References Cited

U.S. PATENT DOCUMENTS

| | | | |
|---|---|---|---|
| 2,033,131 | 10/1936 | Ellis | 106/252 |
| 2,188,882 | 1/1940 | Clocker | 549/253 |
| 2,362,511 | 11/1944 | Teeters | 528/361 |
| 2,683,136 | 7/1954 | Higgins | 528/361 |
| 4,027,676 | 6/1977 | Mattei | 606/230 |
| 4,070,347 | 1/1978 | Schmitt | 528/271 |

FOREIGN PATENT DOCUMENTS 0467226  8/1950  Canada.

*Primary Examiner*—Tae H. Yoon
*Attorney, Agent, or Firm*—Whitham, Curtis, Whitham & McGinn

[57] ABSTRACT

A non-volatile compound useful as a solvent and a method of manufacturing the compound. The compound is formed from heating a combination of a lactide and a drying oil which has conjugated double bonds. The compound is particularly useful as a resin solvent for use with coatings, paints and printing inks. In addition, it can be used as a compatibilizing agent.

10 Claims, No Drawings

NON-VOLATILE SOLVENT REPLACEMENT

BACKGROUND OF THE INVENTION

1. Field of the Invention

The present invention generally relates to a compound which can be used as a solvent and a method of manufacturing the compound. More particularly, it is directed to a compound which is formed from heating a combination of a lactide and a drying oil which has conjugated double bonds. This compound is non-volatile and is particularly useful as a resin solvent for use with coatings, paints and printing inks. It can also be used as a compatibilizing agent for resins.

2. Description of the Prior Art

The formulations of most oil based coatings, paints and printing inks include a solid resin which is dissolved in a solvent. These compounds often contain other ingredients depending on the intended use and desired characteristics. It is common to add pigments or dyes to obtain colored coatings. It is also known to include additives to determine the characteristics of the coating. Some examples of features which can be adjusted include: the gloss level, the mildew resistance, and the adhesive properties.

Solvents are usually organic compounds and are used to alter the physical properties of a compound. The solvents currently in use are generally volatile, causing them to be evaporated into the ambient air. The volatile organic compounds are a major cause of air pollution and therefore, they are subject to a variety of local, state and federal regulations. These regulations and the potential for stricter regulations in the future have prompted the manufacturers of these products to investigate alternatives to these solvents. Although a variety of alternatives have been developed, the majority possess draw backs which have prevented their adoption for general commercial use. The draw backs of the alternatives include poor solvency, high toxicity, short shelf life and the production of toxic by-products.

SUMMARY OF THE INVENTION

It is therefore an object of the present invention to provide a compound which can be used as a solvent and which is non-volatile.

It is another object of the present invention to provide a process for the manufacture of a compound which can be used as a solvent and which is non-volatile.

It is also an object of the present invention to provide a solvent which can dissolve a broad range of resins and is able to form a film.

It is a further object of this invention to provide a compound which is of low toxicity.

It is another object of this invention to provide a solvent for use in coatings, paints and printing inks which can replace organic compounds.

According to the invention, there is provided a method for manufacturing a compound wherein an alpha hydroxy acid, lactic or glycolic acid is heated to remove all of the water. The heating produces a cyclic keto enol tautomer, in the case of lactic acid, a lactide. The lactide is combined with any drying oil which includes conjugated double bonds and the mixture is heated. The resulting product is useful as a solvent and has successfully been combined with a number of resins and other products.

DETAILED DESCRIPTION OF A PREFERRED EMBODIMENT OF THE INVENTION

The process of the present invention produces a compound which is useful as a solvent, for coatings, paints and inks and as a compatibilizing agent. The first step in the production process is to heat a hydroxy carboxylic acid to a temperature at which all the mechanical water and one mole of chemical water per mole of acid is removed. In the preferred embodiment the add is lactic acid, glycolic acid or alpha hydroxy acid. It is most preferred to use lactic acid. The minimum temperature at which the desired amount of water is removed is approximately 150° C. The removal of the water from the acid results in the formation of a cyclic keto enol tautomer. If lactic acid is the starting compound, the product is a lactide which can be represented by one of the following structures:

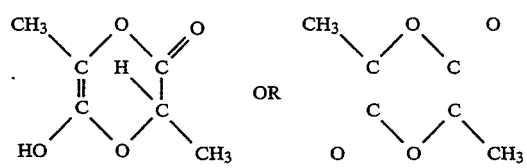

If desired, derivatives of the cyclic keto enol tautomer can be formed by esterification reactions at the site of the hydroxy constituents or by other means. The cyclic keto enol tautomer is then combined with a drying oil which has conjugated double bonds.

It is preferred to use approximately 18% by weight of lactide and approximately 82% by weight of a drying oil or a combination of drying oils. However, the amount of lactide or cyclic keto enol tautomer can range from approximately 5% to 25%. The preferred drying oils include linseed oil, tung oil, oiticica oil, soya oil, dehydrated castor oil, other dehydrated vegetable based oils or other commonly known oils.

The combination of the cyclic keto enol tautomer and drying oil is heated to a temperature of approximately 220° C. for a period of approximately two hours. It is anticipated that different heating schedules could also be employed (e.g., longer times at lower temperatures and shorter times at higher temperatures). The resultant product is characterized as being a liquid which ranges in color from clear amber to straw. The viscosity of the product was measured in a number two zahn cup and was found to be 19 to 26 seconds.

It has been determined that having small quantities of chromium or other transition metals aids in the formation of the product. Specifically, a superior reaction product is obtained when the cyclic keto enol tautomer and drying oil are combined with less than 100 ppm of a transition metal during heating. Optimal results were obtained when approximately 8 - 10 ppm of chromium was present. It has been found that sufficient chromium content for forming the reaction product can be contributed simply by using a stainless steel vessel when heating the cyclic keto enol tautomer and drying oil. By contrast, when a glass reaction vessel was employed, precipitation of solids occurred. A glass reaction vessel might be suitable if a sufficient quantity of chromium salt or other metal complex is added to the reaction mixture.

As an alternative to the two step process of first forming a cyclic keto enol tautomer and then combining the cyclic keto enol tautomer with a drying oil, the reaction product may be formed in a single step by heating a mixture of a drying oil and a hydroxy carboxylic acid that is capable of forming a cyclic keto enol tautomer.

This product is useful as a solvent and can be used with resins and printing inks. In addition, it can also be used to compatibilize polypropylene and polystyrene resins which are used in injection molders and extruders.

The product of the above described process can be used to dissolve resins. In particular, it has been shown to successfully form solutions with hydrocarbons, phenolics, acrylics, styrene acrylic copolymers and alkyd resins. These compounds were preferably approximately 40% by weight of the solution. The solutions which were formed were clear and were able to form hard durable films which ranged in thickness from 0.5 to 2 mils.

The product can also be used in the manufacture of lithographic printing inks. Table 1 provides examples of combinations which can be used to produce printing inks.

TABLE 1

|  | Overprint varnish | Sheetfed web | No heat |
|---|---|---|---|
| Solvent replacement (product) | 65% | 28% | 37% |
| Bodied tung oil | — | 25% | 20% |
| Styrene acrylic copolymer | 31% | — | — |
| Carbon black linseed flush | — | 45% | 40% |
| Micro crystalline wax | — | 2% | 1% |
| Acrylic resin | 4% | — | — |
| Talc | — | — | 2% |

The printing inks manufactured using the product, produced as described supra, were found to create a durable hard film and excellent print quality. The drying time of the inks was between nine and fifteen minutes.

The product of the present invention is also useful as a compatibilizing agent. A mixture of approximately fifty (50) parts of polypropylene, fifty (50) parts of polystyrene and one (1) part of the product was adsorbed on four (4) parts of ethylene propylene styrene terpolymer. The resultant material was extruded to produce a band which as approximately 1.5 millimeters by 12 millimeters. The extruded material was of a uniform consistency and could be bent without breaking. For comparison purposes, the mixture was also prepared without the product and was extruded. This material was not compatibilized and fractured when deformed.

While the invention has been described in terms of the preferred embodiments, those skilled in the art will recognize that the invention can be practiced with modification within the spirit and scope of the appended claims.

I claim:

1. A process for producing a compound, comprising the steps of:

combining approximately 5% to 25% by weight of a cyclic keto enol tautomer formed from a hydroxy carboxylic acid compound having at least one carboxylic acid moiety and one hydroxy moiety with approximately 75% to 95% by weight of at least one drying oil to form a combination of materials; and heating said combination to a temperature sufficient to produce a non-volatile solvent.

2. A process, as recited in claim 1, wherein said cyclic keto enol tautomer is approximately 18% by weight and said drying oil is approximately 82% by weight.

3. A proces, as recited in claim 1, wherein said hydroxy carboxylic acid is selected from the group consisting of alpha hydroxy acid, lactic acid and glycolic acid.

4. A process, as recited in claim 1, wherein said drying oil is selected from the group consisting of linseed oil, tung oil, oiticica oil, soya oil, dehydrated castor oil, dehydrated vegetable oil, and any combination thereof.

5. A process, as recited in claim 1, wherein said cyclic keto enol tautomer is a lactide.

6. A process for producing a compound, comprising the steps of:

combining approximately 5% to 25% by weight of a cyclic keto enol tautomer with approximately 75% to 95% by weight of at least one drying oil to form a combination of materials; and heating said combination to a temperature sufficient to produce a non-volatile solvent, said heating step is performed with said cyclic keto enol tautomer and said drying oil in the presence of a transition metal.

7. A process, as recited in claim 6, wherein said transition metal is chromium.

8. A process, as recited in claim 1, wherein said combining step includes forming said cyclic keto enol tautomer with heating.

9. A compound produced by the process of combining approximately 5% to 25% by weight of a cyclic keto enol tautomer formed from a hydroxy carboxylic acid compound having at least one carboxylic acid moiety and one hydroxy moiety with approximately 75% to 95% by weight of at least one drying oil to form a combination of materials and heating said combination to a temperature sufficient to produce a non-volatile solvent.

10. A compound produced by the process of combining approximately 5% to 25% by weight of a cyclic keto enol tautomer formed from a hydroxy carboxylic acid compound having at least one carboxylic acid moiety and one hydroxy moiety with approximately 75% to 95% by weight of at least one drying oil to form a combination of materials and heating said combination in the presence of a transition metal to a temperature sufficient to produce a non-volatile solvent.

* * * * *

UNITED STATES PATENT AND TRADEMARK OFFICE
CERTIFICATE OF CORRECTION

PATENT NO.: 5,405,935

DATED: April 11, 1995

INVENTOR(S): David Westerhoff

It is certified that error appears in the above-identified patent and that said Letters Patent is hereby corrected as shown below:

In column 2, lines 20-25 please delete the formulas which appear and insert the following:

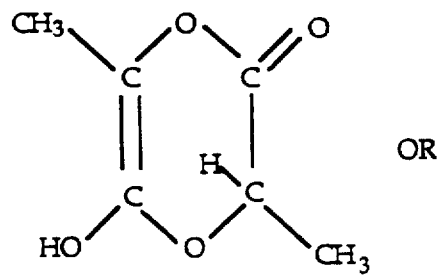 OR 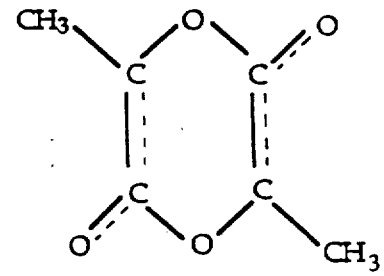

Signed and Sealed this

Fifth Day of December, 1995

Attest:

BRUCE LEHMAN

Attesting Officer     Commissioner of Patents and Trademarks